(12) United States Patent
Inouye et al.

(10) Patent No.: US 11,992,220 B2
(45) Date of Patent: *May 28, 2024

(54) OCCLUSIVE MEDICAL DEVICE WITH FIXATION MEMBERS

(71) Applicant: BOSTON SCIENTIFIC SCIMED, INC., Maple Grove, MN (US)

(72) Inventors: Joshua Mark Inouye, Maple Grove, MN (US); Brian Joseph Tischler, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/708,864

(22) Filed: Mar. 30, 2022

(65) Prior Publication Data

US 2022/0218356 A1 Jul. 14, 2022

Related U.S. Application Data

(63) Continuation of application No. 16/362,867, filed on Mar. 25, 2019, now Pat. No. 11,331,103.

(Continued)

(51) Int. Cl.
*A61B 17/12* (2006.01)
*A61B 17/00* (2006.01)

(52) U.S. Cl.
CPC .. *A61B 17/12122* (2013.01); *A61B 17/12031* (2013.01); *A61B 17/12172* (2013.01);

(Continued)

(58) Field of Classification Search
CPC ........ A61B 17/12022; A61B 17/12031; A61B 17/12122; A61B 17/12172;
(Continued)

(56) References Cited

U.S. PATENT DOCUMENTS 5,800,526 A 9/1998 Anderson et al.
6,231,561 B1 5/2001 Frazier et al.
(Continued)

FOREIGN PATENT DOCUMENTS

CN 1399571 A 2/2003
CN 203226856 U 10/2013
(Continued)

OTHER PUBLICATIONS

Cline, "File: Fish hooks.jpg," Wikipedia foundation, Inc., San Francisco, CA, Jun. 2007; p. 1 of 4; available online at http://en.wikipedia.org/wiki/File:Fish_hooks.jpg; last accessed Oct. 5, 2012.
(Continued)

*Primary Examiner* — Katherine M Rodjom
(74) *Attorney, Agent, or Firm* — Seager, Tufte & Wickhem LLP (57) ABSTRACT

An example occlusive implant is disclosed. The example occlusive implant includes an expandable framework configured to shift between a collapsed configuration and an expanded configuration, wherein the expandable framework includes a plurality of strut members circumferentially spaced around a longitudinal axis of the expandable framework, wherein one or more of the plurality of strut members includes a first twisted portion and a face portion. The occlusive implant also includes a plurality of fixation members disposed along the face portion of one or more of the plurality of strut members.

20 Claims, 7 Drawing Sheets

Related U.S. Application Data (60) Provisional application No. 62/649,954, filed on Mar. 29, 2018.

(52) U.S. Cl.
CPC .............. *A61B 17/12177* (2013.01); *A61B 2017/00243* (2013.01); *A61B 2017/00526* (2013.01); *A61B 2017/00579* (2013.01); *A61B 2017/00867* (2013.01)

(58) Field of Classification Search
CPC ... A61B 17/12177; A61B 2017/005791; A61F 2/848; A61F 2002/8483; A61F 2002/8486
See application file for complete search history.

(56) References Cited

U.S. PATENT DOCUMENTS

| | | | |
|---|---|---|---|
| 6,443,972 B1* | 9/2002 | Bosma | A61F 2/0108 606/200 |
| 7,727,189 B2 | 6/2010 | VanTassel et al. | |
| 7,748,389 B2 | 7/2010 | Salahieh et al. | |
| 7,972,359 B2 | 7/2011 | Kreidler | |
| 8,221,384 B2 | 7/2012 | Frazier et al. | |
| 8,372,143 B2 | 2/2013 | Majercak et al. | |
| 8,562,509 B2 | 10/2013 | Bates | |
| 2003/0208214 A1 | 11/2003 | Loshakove et al. | |
| 2004/0117004 A1 | 6/2004 | Osborne et al. | |
| 2004/0220682 A1 | 11/2004 | Levine et al. | |
| 2005/0125020 A1 | 6/2005 | Meade et al. | |
| 2009/0005803 A1 | 1/2009 | Batiste | |
| 2009/0099596 A1 | 4/2009 | McGuckin, Jr. et al. | |
| 2010/0016953 A1 | 1/2010 | Sisken et al. | |
| 2010/0312269 A1 | 12/2010 | McGuckin, Jr. et al. | |
| 2010/0324595 A1 | 12/2010 | Linder et al. | |
| 2011/0054515 A1 | 3/2011 | Bridgeman et al. | |
| 2011/0178534 A1 | 7/2011 | Whitman et al. | |
| 2012/0172654 A1 | 7/2012 | Bates | |
| 2012/0245619 A1 | 9/2012 | Guest et al. | |
| 2012/0316584 A1 | 12/2012 | Miles et al. | |
| 2013/0073029 A1 | 3/2013 | Shaw | |
| 2013/0178889 A1 | 7/2013 | Miles et al. | |
| 2014/0135817 A1* | 5/2014 | Tischler | A61B 17/0057 29/428 |
| 2014/0188157 A1 | 7/2014 | Clark | |
| 2014/0277562 A1* | 9/2014 | Seddon | A61F 2/915 219/121.72 |
| 2015/0005809 A1 | 1/2015 | Ayres et al. | |
| 2016/0331382 A1 | 11/2016 | Center et al. | |
| 2017/0156840 A1 | 6/2017 | Edmiston et al. | |

FOREIGN PATENT DOCUMENTS

| | | |
|---|---|---|
| CN | 105208977 A | 12/2015 |
| EP | 1595504 A1 | 11/2005 |
| EP | 2481381 A1 | 8/2012 |
| EP | 2967930 B1 | 11/2018 |
| JP | 2003532457 A | 11/2003 |
| JP | 2005324019 A | 11/2005 |
| JP | 2007513684 A | 5/2007 |
| WO | 0035352 A1 | 6/2000 |
| WO | 03032818 A2 | 4/2003 |
| WO | 2007044536 A2 | 4/2007 |
| WO | 2010148246 A2 | 12/2010 |
| WO | 2014106239 A1 | 7/2014 |

OTHER PUBLICATIONS

International Search Report and Written Opinion dated Apr. 22, 2014 for International Application No. PCT/US2013/078454.
Aryana et al., "Incomplete Closure of the Left Atrial Appendage: Implication and Management." Curr Cardiol Rep., 18(9):82, 2016.
Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.
University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.
Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.
International Search Report and Written Opinion dated Jun. 28, 2019 for International Application No. PCT/US2019/023807.

* cited by examiner

OCCLUSIVE MEDICAL DEVICE WITH FIXATION MEMBERS

CROSS-REFERENCE TO RELATED APPLICATIONS

This application is a continuation of U.S. application Ser. No. 16/362,867, filed Mar. 25, 2019, which claims the benefit of priority under 35 U.S.C. § 119 to U.S. Provisional Application Ser. No. 62/649,954, filed Mar. 29, 2018, the entirety of which is incorporated herein by reference

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to control thrombus formation within the left atrial appendage of patients suffering from atrial fibrillation.

SUMMARY

An example occlusive implant includes an expandable framework configured to shift between a collapsed configuration and an expanded configuration, wherein the expandable framework includes a plurality of strut members circumferentially spaced around a longitudinal axis of the expandable framework, wherein one or more of the plurality of strut members includes a first twisted portion and a face portion. The occlusive implant also includes a plurality of fixation members disposed along the face portion of one or more of the plurality of strut members.

In addition or alternatively, wherein the fixation members and the expandable framework are formed from a unitary tubular member.

In addition or alternatively, wherein one or more of the plurality of fixation members extends radially away from the longitudinal axis.

In addition or alternatively, wherein each of the plurality of strut members includes 8 or more fixation members disposed thereon.

In addition or alternatively, wherein the plurality of fixation members are positioned adjacent to the twisted portion of each of the strut members.

In addition or alternatively, wherein the one or more of the strut members includes a second twisted portion, and wherein the face portion is positioned between the first twisted portion and the second twisted portion.

In addition or alternatively, wherein the plurality of fixation members are formed by laser cutting.

In addition or alternatively, wherein the twisted portion is formed by a heat setting the one or more of the plurality of strut members.

In addition or alternatively, wherein the face portion of one or more of the plurality of strut members includes a curved region, and wherein the curved region is configured to extend radially away from the longitudinal axis of the expandable framework.

In addition or alternatively, wherein the curved region includes an apex, and wherein at least one of the plurality of fixation members is disposed along the apex of the curved region.

Another occlusive implant includes:
an expandable framework configured to shift between a collapsed configuration and an expanded configuration, wherein the expandable framework includes a plurality of strut members circumferentially spaced around a longitudinal axis of the expandable framework, wherein one or more of the plurality of strut members includes a first twisted portion and a face portion;
a plurality of fixation members disposed along the face portion of one or more of the plurality of strut members; and
an occlusive member disposed along an outer surface of the expandable framework.

In addition or alternatively, wherein the fixation members and the expandable framework are formed from a unitary tubular member.

In addition or alternatively, wherein one or more of the plurality of fixation members extends radially away from the longitudinal axis.

In addition or alternatively, wherein each of the plurality of strut members includes four or more fixation members disposed thereon.

In addition or alternatively, wherein the one or more of the strut members includes a second twisted portion, and wherein the face portion is positioned between the first twisted portion and the second twisted portion.

In addition or alternatively, wherein the occlusive member extends circumferentially around the outer surface of the occlusive member.

In addition or alternatively, wherein at least a portion of the plurality of fixation members extend through an aperture formed in the occlusive member.

In addition or alternatively, wherein the face portion of one or more of the plurality of strut members includes a curved region, and wherein the curved region is configured to extend radially away from the longitudinal axis of the expandable framework.

In addition or alternatively, wherein the curved region includes an apex, and wherein at least one of the plurality of fixation members is disposed along the apex of the curved region.

A method for manufacturing an occlusive implant includes:
laser cutting an expandable framework from a tubular member, wherein the laser cutting forms a plurality of strut members and a plurality of fixation members disposed along the plurality of strut members, and wherein the plurality of strut members and the plurality of fixation members extend circumferentially around a longitudinal axis of the tubular member;

rotating at least some of the plurality of strut members such that the plurality of fixation members extend radially away from the longitudinal axis, and wherein rotating each of the strut members forms a twist in the strut member; and expanding the expandable framework radially outward; and disposing an occlusive member along the outer surface of the expandable framework.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thrombolytic material entering the blood stream from the left atrial appendage. Example medical devices and/or occlusive implants that close off the left atrial appendage are disclosed herein.

Figure 1:
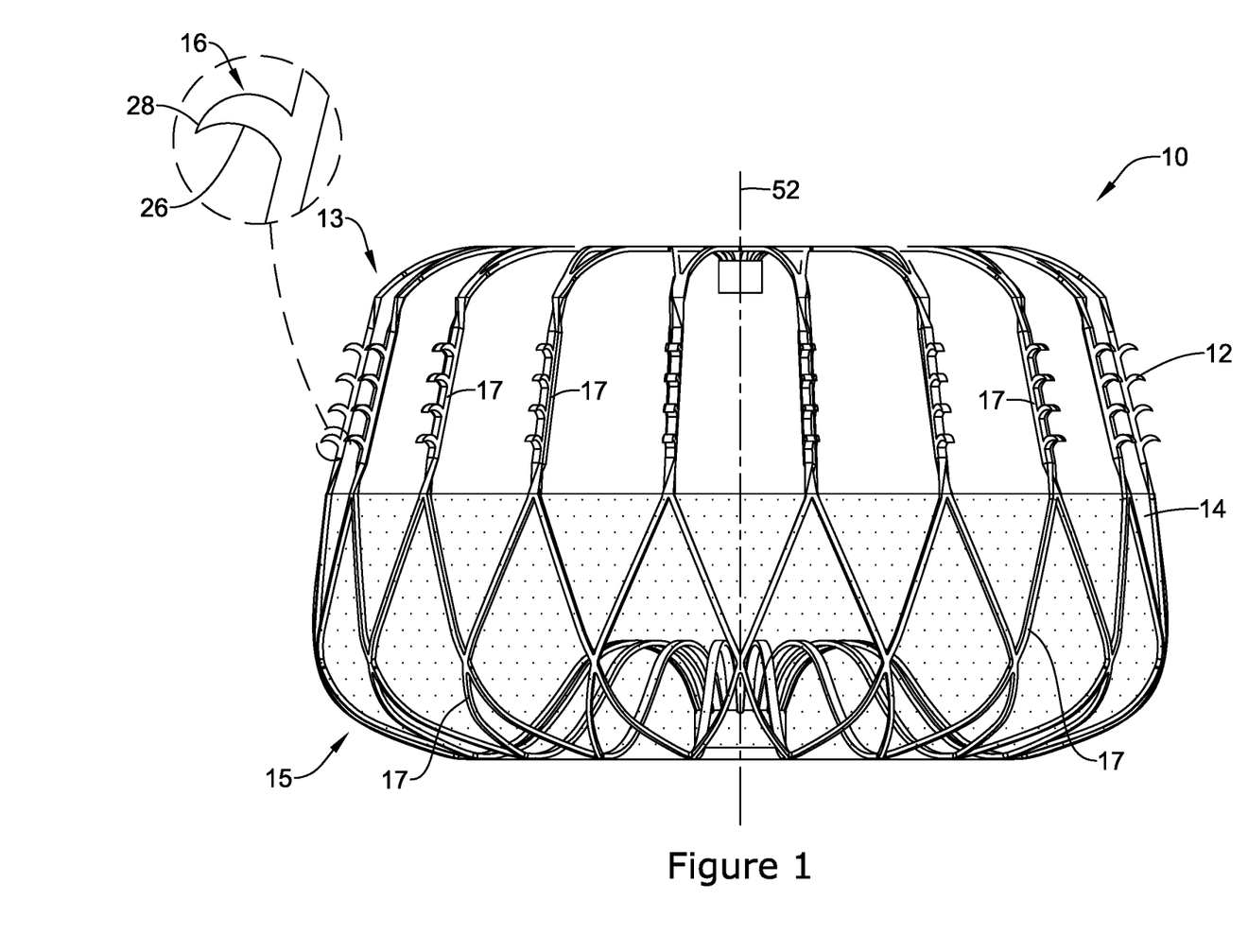
FIG. 1 is a plan view of an example occlusive implant.

FIG. 1 illustrates an example occlusive implant 10. The implant 10 may include an expandable framework 12. The expandable framework 12 may include a first end region 13 and a second end region 15. Additionally, the expandable framework 12 may include a plurality of strut members 17. The strut members 17 may be interconnected with one another and extend circumferentially around the longitudinal axis 52 to define the expandable framework 12 of the occlusive implant 10.

The occlusive implant 10 may also include an occlusive member 14 disposed on, disposed over, disposed about, or covering at least a portion of the expandable framework 12. In some embodiments, the occlusive member 14 may be disposed on, disposed over, disposed about or cover at least a portion of an outer (or outwardly-facing) surface of the expandable framework 12. FIG. 1 further illustrates that the occlusive member 14 may extend only partially along the longitudinal extent of the expandable framework 12. However, this is not intended to be limiting. Rather, the occlusive member 14 may extend along the longitudinal extent of the expandable framework to any degree (e.g., the full longitudinal extend of the expandable framework 12).

In some embodiments, the occlusive member 14 may be permeable or impermeable to blood and/or other fluids, such as water. In some embodiments, the occlusive member 14 may include a woven, braided and/or knitted material, a fiber, a sheet-like material, a fabric, a polymeric membrane, a metallic or polymeric mesh, a porous filter-like material, or other suitable construction. In some embodiments, the occlusive member 14 may prevent thrombi (i.e. blood clots, etc.) from passing through the occlusive member 14 and out of the left atrial appendage into the blood stream. In some embodiments, the occlusive member 14 may promote endothelization after implantation, thereby effectively removing the left atrial appendage from the patient's circulatory system. Some suitable, but non-limiting, examples of materials for the occlusive member 14 are discussed below.

As will be discussed in greater detail below, FIG. 1 further illustrates that the expandable framework 12 may include a plurality of fixation members 16 disposed about a periphery of the expandable framework 12. For example, FIG. 1 shows that the fixation members 16 may be disposed along one or more of the strut members 17 which define the expandable framework 12. Some suitable, but non-limiting, examples of materials for the expandable framework 12 and/or the plurality of anchor members 16 are discussed below. The plurality of fixation members 16 may extend radially outward from the strut members 17 of the expandable framework 12. In other words, the plurality of fixation members 16 may extend radially away from the longitudinal axis 52 of the expandable framework 12.

As shown in the detailed view of FIG. 1, at least some of the plurality of fixation members 16 may each have and/or include a body portion 26 and a tip portion 28. Further, the body portion 26 of some of the plurality of fixation members 16 (such as the fixation member 16 shown in the detailed view of FIG. 1) may be curved. As will be discussed in greater detail below, the plurality of fixation member 16 may be curved such that the tip portion 28 points toward the second end region 15 of the expandable framework 12. However, this is not intended to be limiting. Rather, it is contemplated that one or more of the fixation members may point toward the first end region 13 or in a direction other than toward the second end region 15. Additionally, the shape of the fixation members 16 illustrated in FIG. 1 is non-limiting. Rather, it is contemplated that the fixation members 16 may include a variety of different shapes, geometries, etc.

Each of the individual fixation members 16 may have a "height" (e.g., the length of the fixation member 16 from its tip portion 28 to the base of its body portion 26) of about 0.005" to about 0.060", or, in some instances, about 0.025". However, the height of each fixation member 16 may be dependent on how many total fixation members 16 are positioned on the expandable framework 12. For example, a greater the number of fixation members 16 on an expandable framework 12 may correspond a lower the height of each individual fixation member 16. Conversely, the height of each individual fixation member 16 may be greater for example framework 12 designs which include relatively fewer fixation members 16.

As will be discussed in greater detail below, the expandable framework 12 and the plurality of fixation members 16 may be integrally formed and/or cut from a unitary member. In some embodiments, the expandable framework 12 and the plurality of fixation members 16 may be integrally formed and/or cut from a unitary tubular member and subsequently formed and/or heat set to a desired shape in the expanded configuration. In some embodiments, the expandable framework 12 and the plurality of fixation members 16 may be integrally formed and/or cut from a unitary flat member, and then rolled or formed into a tubular structure and subsequently formed and/or heat set to the desired shape in the expanded configuration. Some exemplary means and/or methods of making and/or forming the expandable framework 12 include laser cutting, machining, punching, stamping, electro discharge machining (EDM), chemical dissolution, etc. Other means and/or methods are also contemplated.

As illustrated in FIG. 1, the plurality of fixation members 16 disposed along the expandable framework 12 may include several "rows" of fixation members 16 disposed along the strut members 17. For example, the expandable framework 12 may include several fixation members 16 disposed along several strut members 17. For example, in some instances one or more strut members 17 may include 1, 2, 3, 4, 5, 6, 7, 8, 9, 10, 15, 20, 25, 30, 40, 45, 50 or more fixation members 16 disposed thereon. Additionally, one or more of the fixation members 16 may extend through the occlusive member 14.

Figure 2:
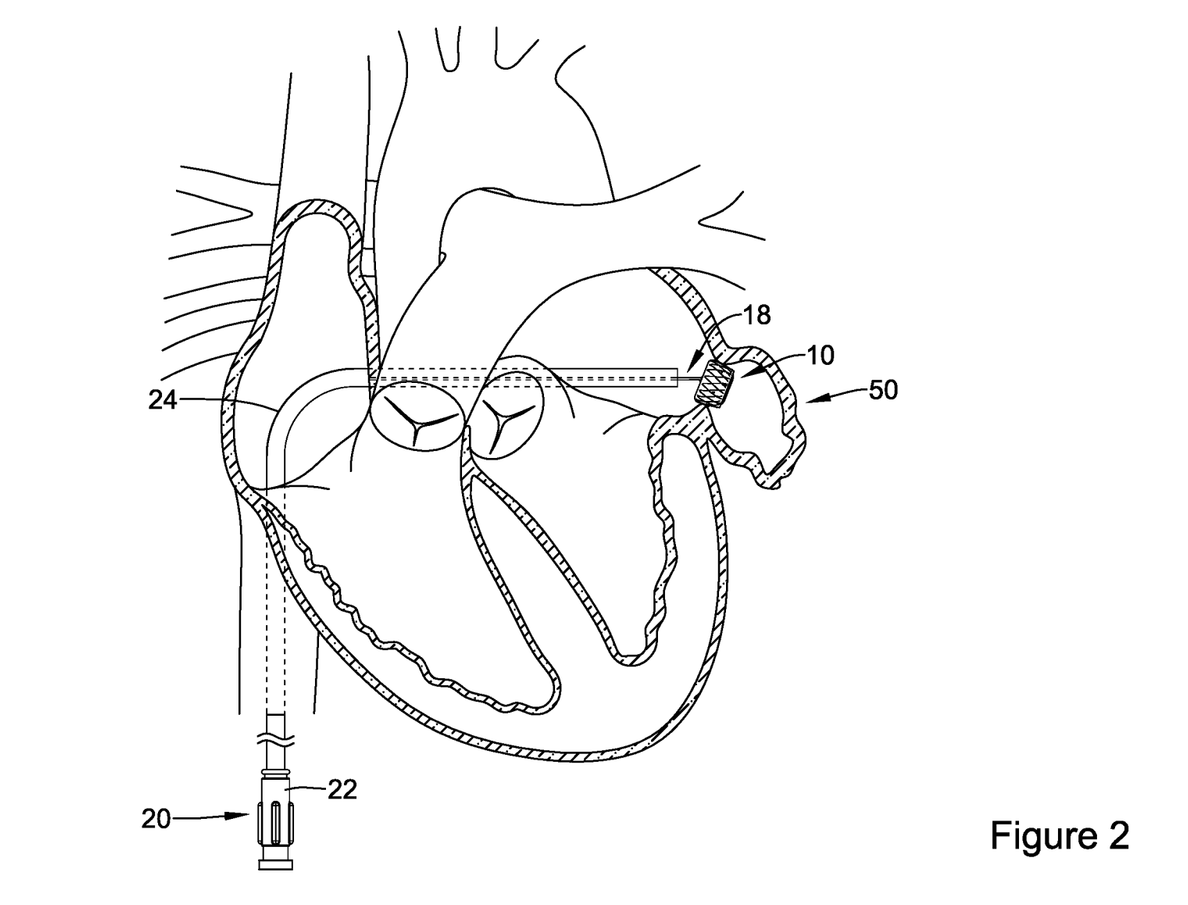
FIG. 2 shows an example occlusive implant positioned in the heart.

FIG. 2 illustrates that the occlusive implant 10 may be inserted and advanced through a body lumen via an occlusive implant delivery system 20. FIG. 2 further illustrates the occlusive implant 10 being delivered and positioned within the left atrial appendage 50. In some instances, an occlusive implant delivery system 20 may include a delivery catheter 24 which is guided toward the left atrium via various chambers and lumens of the heart (e.g., the inferior vena cava, the right atrium, etc.) to a position adjacent the left atrial appendage 50.

The delivery system 20 may include a hub member 22 coupled to a proximal region of the delivery catheter 24. The hub member 22 may be manipulated by a clinician to direct the distal end region of the delivery catheter 24 to a position adjacent the left atrial appendage 50. In some embodiments, an occlusive implant delivery system may include a core wire 18. Further, a proximal end of the expandable framework 12 may be configured to releasably attach, join, couple, engage, or otherwise connect to the distal end of the core wire 18. In some embodiments, an end region of the expandable framework 12 may include a threaded insert coupled thereto. In some embodiments, the threaded insert may be configured to and/or adapted to couple with, join to, mate with, or otherwise engage a threaded member disposed at the distal end of a core wire 18. Other means of releasably coupling and/or engaging the proximal end of the expandable framework 12 to the distal end of the core wire 18 are also contemplated.

Figure 3:
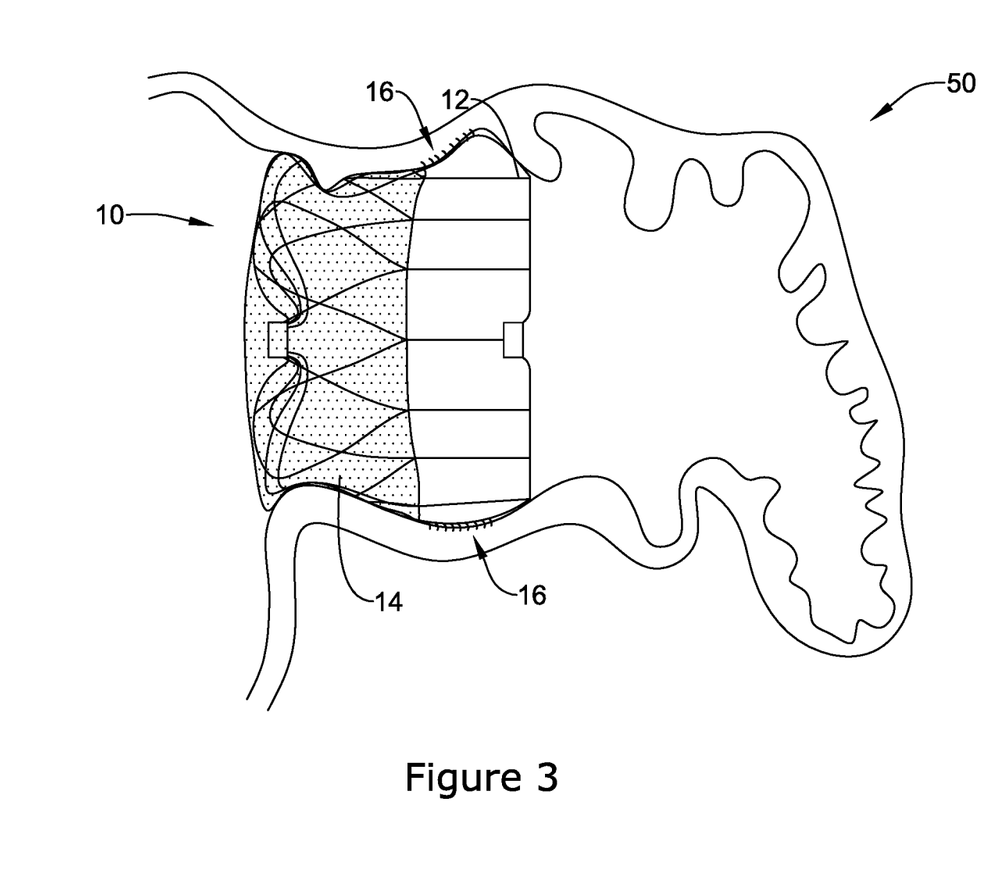
FIG. 3 shows an example occlusive implant positioned in the left atrial appendage.

FIG. 3 illustrates a left atrial appendage occlusive implant 10 positioned adjacent the left atrial appendage 50 via the delivery catheter 24 (described above with respect to FIG. 2). As discussed above, in some examples, the occlusive implant 10 may be configured to shift between a collapsed configuration and an expanded configuration. For example, in some instances, the occlusive implant 10 may be in a collapsed configuration during delivery via an occlusion implant delivery system, whereby the occlusive implant 10 expands to an expanded configuration once deployed from the occlusion implant delivery system.

Additionally, FIG. 3 illustrates that the expandable framework 12 may be compliant and, therefore, substantially conform to and/or be in sealing engagement with the shape and/or geometry of a lateral wall of a left atrial appendage in the expanded configuration. In some embodiments, the occlusive implant 10 may expand to a size, extent, or shape less than or different from a maximum unconstrained extent, as determined by the surrounding tissue and/or lateral wall of the left atrial appendage. Additionally, FIG. 3 illustrates that the expandable framework 12 may be held fixed adjacent to the left atrial appendage by one or more fixation members 16.

Further, it can be appreciated that the elements of the expandable framework 12 may be tailored to increase the flexibility and compliance of the expandable framework 12 and/or the occlusive implant 10, thereby permitting the expandable framework 12 and/or the occlusive implant 10 to conform to the tissue around it, rather than forcing the tissue to conform to the expandable framework 12 and/or the occlusive implant 10. Additionally, in some instances, it may be desirable to design the occlusive implant 10 discussed above to include various features, components and/or configurations which improve the sealing capabilities of the occlusive implant within the left atrial appendage.

As discussed above, the expandable implant 10 illustrated in FIG. 1 (including the expandable framework 12 and fixation members 16) may be formed from a unitary member. For example, in some examples the expandable framework 12 may be formed by laser cutting a unitary member into a desired geometry and then expanding the unitary member to form the expendable framework 12 illustrated in FIG. 1. Additionally, it can be appreciated that a utilizing a particular manufacturing methodology (e.g., laser cutting) may permit the expandable framework 12 to include "micro" elements. For example, in some examples the plurality of fixation members 16 may be described as "microbarbs" or "microfixation" elements. These elements may be very small as compared to the overall size of the expandable framework 12. However, even though they may be relatively small, collectively, they may be able to engage the tissue of the left atrial appendage with the same or greater force as larger (but fewer) anchoring members.

Figure 4:
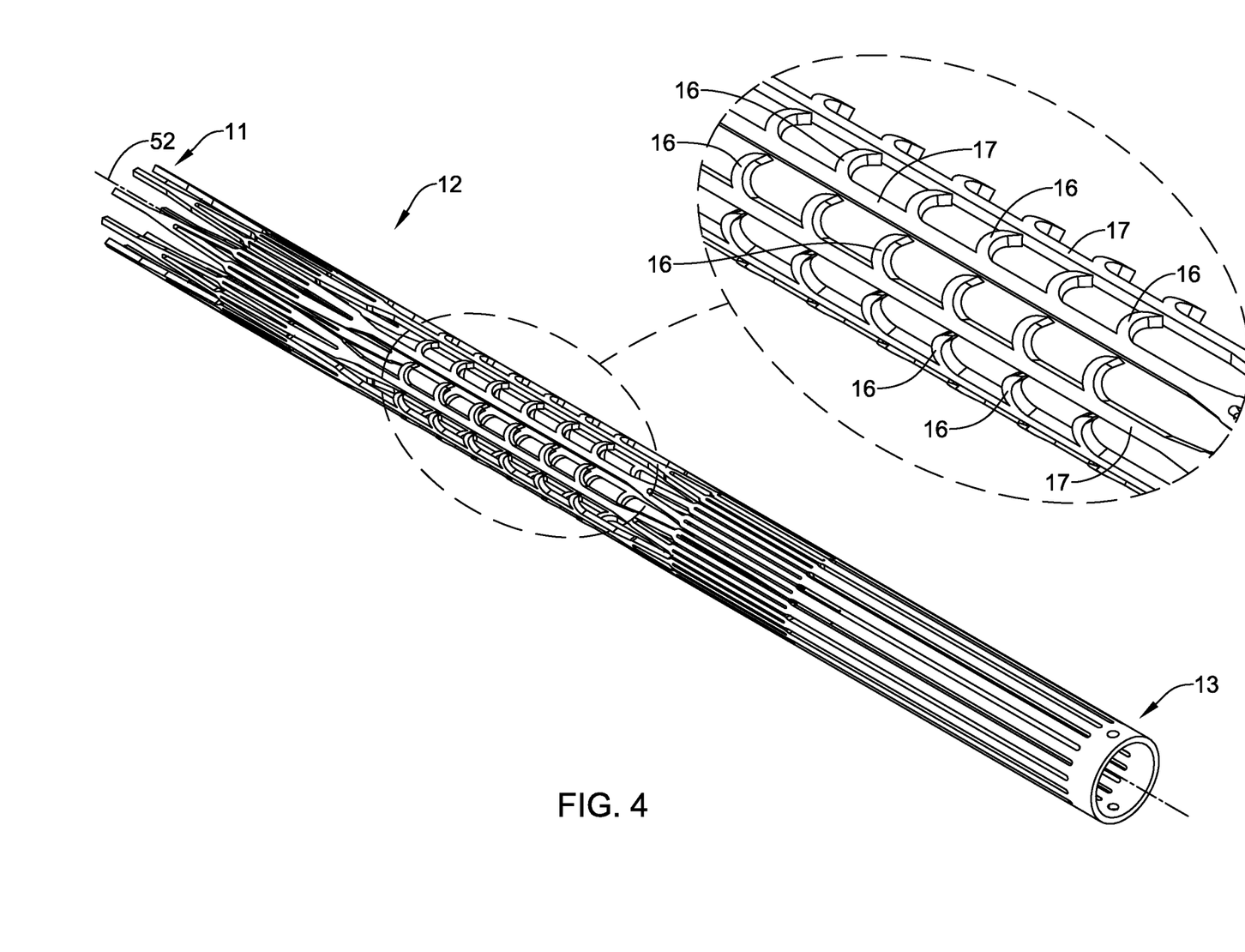
FIG. 4 illustrates an example occlusive implant.

FIG. 4 illustrates an initial manufacturing step (in a sequence of steps) utilized to form the expandable framework 12 (discussed above with respect to FIGS. 1-3). For example, FIG. 4 illustrates the expandable framework 12 in an unexpanded configuration after having been laser cut from a unitary member (e.g., a tubular member), but prior to being expanded to the configuration shown in FIG. 1. As shown in FIG. 4, the expandable framework 12 includes the first end region 11, the second end region 13 and the longitudinal axis 52. Further, it is noted that the expandable framework 12 shown in FIG. 4 does not include the occlusive member 14 (shown above). Additionally, the detailed view of FIG. 4 illustrates the struts 17 of the expandable framework 12 which includes the plurality of fixation members 16. As shown in FIG. 4, the tubular member (from which the expandable framework 12 is laser cut, for example) may be machined (e.g., laser cut) such that the fixation members 16 are formed as unitary elements of the strut members 17. Further, each of the fixation members 16 may be laser cut to include the body portion 26 and the tip portion 28 (described above with respect to FIG. 1).

Additionally, one advantage to utilizing a manufacturing process such as laser cutting to form the fixation members 16 is that it may be possible to reduce the size of the tubular member from which the expandable framework 12 may be cut. For example, FIG. 4 illustrates the fixation members 16 circumferentially aligned with the curvature of the outer surface of the tubular member. In other words, the laser cutting process may remove material between the strut members 17 and/or the fixation members 16. The remaining material (e.g., the struts 17 and the fixation members 16, for example) are simply what is left of the tubular member after laser cutting. Therefore, the laser cutting process may permit structure of the expandable framework 12 to be formed in a geometrically "tight" pattern. In other words, laser cutting the struts 17 and/or the fixation members 16 may permit the fixation members 16 to be tightly nested between the struts 17 in a spatially "efficient" pattern and/or geometry.

Figure 5:
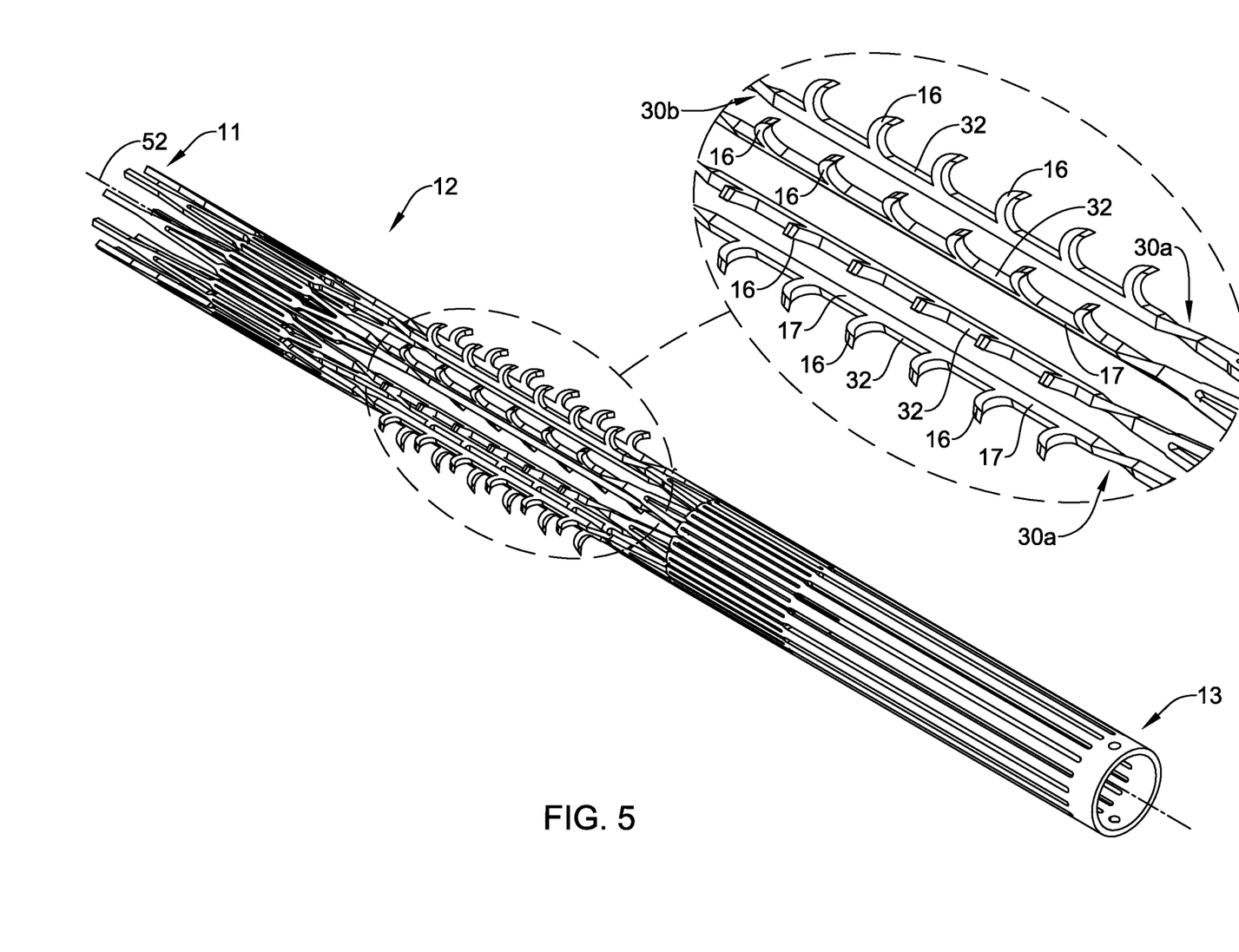
FIG. 5 illustrates another example occlusive implant.

FIG. 5 shows another manufacturing step in the sequence of steps to form the expandable framework 12 from a solid tubular member. In particular, FIG. 5 illustrates a manufacturing step occurring after the laser cutting step discussed and illustrated with respect to FIG. 4. Specifically, comparison of the expandable framework 12 shown in FIG. 5 to that shown in FIG. 4 illustrates each of the plurality of strut members 17 after having have been rotated (e.g., twisted) 90 degrees. Further, the detailed view of FIG. 5 illustrates twisted regions 30a, 30b of each of the strut members 17. In some examples, each of the strut members 17 may include a first twisted region 30a and a second twisted region 30b. The first twisted region 30a may be spaced away from the second twisted region 30b. It can be appreciated that the 90 degree rotation of the strut members 17 also rotates each of the plurality of fixation members 16 90 degrees. Further, the rotation of the fixation members 16 results in positioning each of the fixation members such that they are extending radially away from the longitudinal axis 52 of the expandable framework 12. For example, the detailed view of FIG. 5 illustrates each of the fixation members 16 extending radially away from a face portion 32 of each of the strut members 17. It can be appreciated that this rotated position permits the fixation members 16 to engage with the tissue surrounding the left atrial appendage upon deployment of the occlusive member within the left atrial appendage.

Additionally, the rotation described above may be induced by a heat setting manufacturing step (e.g., in nitinol processing) to twist the strut or plastically deforming the strut without heat setting (e.g., for materials such as stainless steel). For example, the strut members 17 (including the fixation members 16) may be "heat set" into the configuration shown in FIG. 5 (e.g., after having been twisted 90 degrees such that the fixation members 16 extend radially away from the longitudinal axis). Heat setting the strut members 17 may permit the strut members 17 to shift between the configuration shown in FIG. 4 (e.g., the configuration in which the fixation members 16 are positioned in a circumferential direction) and the configuration shown in FIG. 5 (e.g., the configuration of the struts 17 after having been twisted 90 degrees such that the fixation members 16 extend radially away from the longitudinal axis).

Figure 6:
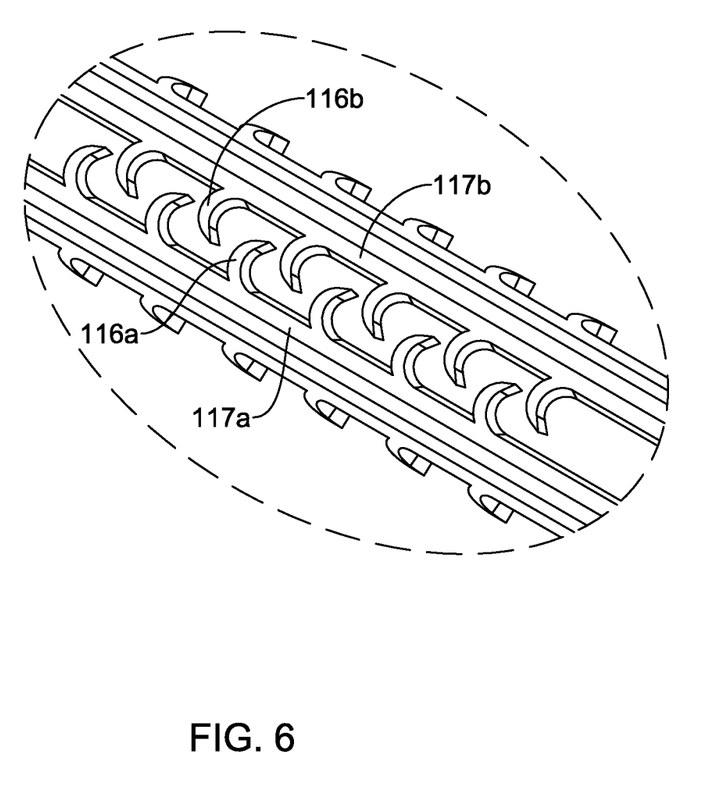
FIG. 6 illustrates another example occlusive implant.

FIG. 6 illustrates another example of the expandable framework 12 in an unexpanded configuration after having been laser cut from a unitary member (e.g., a tubular member), but prior to being expanded to the configuration shown in FIG. 1. As shown in FIG. 6, the expandable framework 12 includes a first strut 117a positioned adjacent a second strut 117b. Each of the first strut 117a and the second strut 117b include fixation member 116a and fixation member 116b, respectively. Further, FIG. 6 illustrates that the fixation members 116a and 116b are cut such that the first fixation member 116a and the second fixation member 116b face opposing directions relative to one another. Further, the struts 117a and 117b and corresponding fixation members 116a and 116b are laser cut such that the fixation members 116a and 116b may nest (e.g., interdigitate) with one another. It can be appreciated that this pattern may permit the expandable framework 16 to be formed (e.g., laser cut) from a tubular member having a diameter (and corresponding surface area) which is less than that of the tubular member shown in FIG. 4 because the fixation members 116a and 116b may be able to be nested closer together. Further, it can be appreciated that each of the first strut 117a and the second strut 117b may be rotated such that the fixation members 116a and 116b extend radially away from the longitudinal axis (as described above with respect to FIG. 5). However, in FIG. 6, the strut member 117a and the strut member 117b may have to be rotated in opposite directions, respectively, to achieve the expanded configuration of the expendable member shown in FIG. 1.

Figure 7:
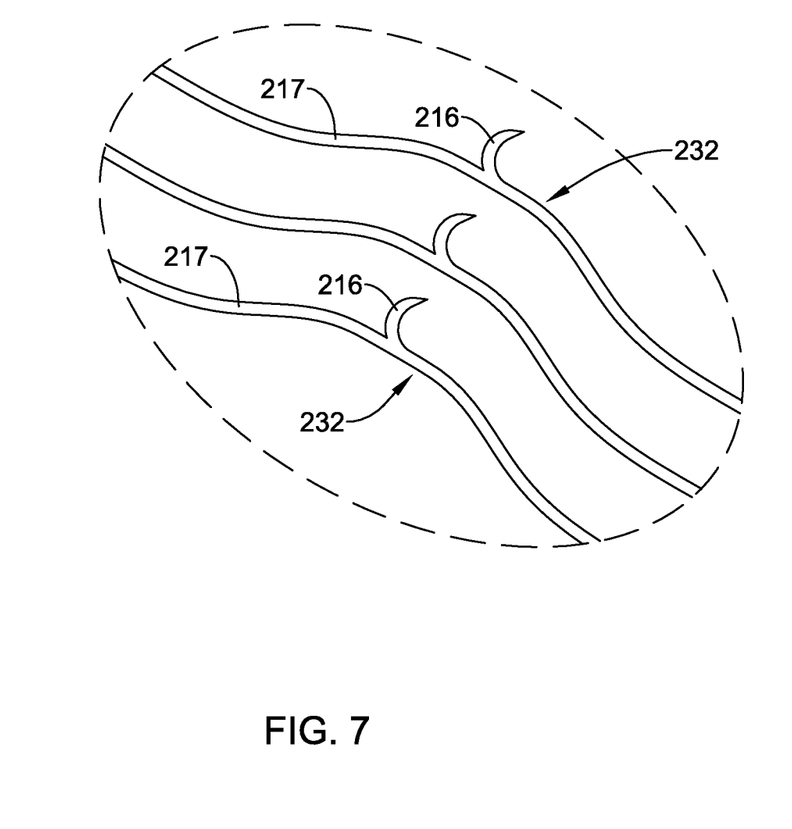
FIG. 7 illustrates another example occlusive implant.

FIG. 7 illustrates another example of the expandable framework 12 in an unexpanded configuration after having been laser cut from a unitary member (e.g., a tubular member), but prior to being expanded to the configuration shown in FIG. 1. As shown in FIG. 7, the expandable framework 12 may include a plurality of strut members 217 positioned adjacent to one another. FIG. 7 shows the struts 217 positioned in a circumferential direction after having been laser cut from a tubular member (similar to the configuration shown in FIG. 4). Additionally, each of the strut members 217 may include a curved region. Further, the curved region may include an apex portion 232. As illustrated in FIG. 7, a fixation member 216 may be disposed along the apex portion 232 of the curved region of each of the struts 217.

Additionally, it can be appreciated that the struts 217 shown in FIG. 7 may be rotated similarly to the struts described above with respect to FIG. 5. In other words, the struts may be rotated 90 degrees such that the fixation members 216 extend radially away from the longitudinal axis of the expandable framework. However, it can be further appreciated that the curved region of the strut member 217 may project the fixation members 216 radially outward to a greater extent than if the strut members 217 did not include a curved region. In other words, the curved regions of the struts 217 may provide a radial prominence to the struts 217 such that they project the fixation members 216 radially outward (as they engage the tissue of the left atrial appendage) to a greater extent than if the strut members 217 did not include a curved region.

The materials that can be used for the various components of the occlusive implant 10 (and variations, systems or components thereof disclosed herein) and the various elements thereof disclosed herein may include those commonly associated with medical devices. For simplicity purposes, the following discussion makes reference to the occlusive implant 10 (and variations, systems or components disclosed herein). However, this is not intended to limit the devices and methods described herein, as the discussion may be applied to other elements, members, components, or devices disclosed herein.

In some embodiments, the occlusive implant 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 (and variations, systems or components thereof disclosed herein). to achieve the same result.

In some embodiments, a degree of Magnetic Resonance Imaging (MM) compatibility is imparted into the occlusive implant 10 (and variations, systems or components thereof disclosed herein). For example, the occlusive implant 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive implant 10 (and variations, systems or components disclosed herein) or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive implant 10 (and variations, systems or components thereof disclosed herein) and/or portions thereof, may be made from or include a polymer or other suitable material. Some examples of suitable polymers may include copolymers, polyisobutylene-polyurethane, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

The invention claimed is:

1. An occlusive implant, comprising:
   an expandable framework configured to shift between a collapsed configuration and an expanded configuration, wherein the expandable framework includes a plurality of strut members circumferentially spaced around a longitudinal axis of the expandable framework, wherein one or more of the plurality of strut members includes a first twisted portion, a second twisted portion, and a face portion extending therebetween, wherein in the expanded configuration, an entirety of the face portion extends linearly between the first twisted portion and the second twisted portion; and a plurality of fixation members disposed along the face portion of one or more of the plurality of strut members;

wherein in the collapsed configuration, a first plurality of fixation members disposed along a first face portion are longitudinally offset and circumferentially interdigitated with a second plurality of fixation members disposed along an adjacent second face portion.

2. The occlusive implant of claim 1, wherein the plurality of fixation members and the expandable framework are formed from a unitary tubular member.

3. The occlusive implant of claim 1, wherein one or more of the plurality of fixation members extends radially away from the face portion.

4. The occlusive implant of claim 1, wherein each of the plurality of strut members includes 8 or more fixation members disposed thereon.

5. The occlusive implant of claim 1, wherein the plurality of fixation members are positioned adjacent to the first and second twisted portion of each of the strut members.

6. The occlusive implant of claim 1, wherein the plurality of fixation members are formed by laser cutting.

7. The occlusive implant of claim 1, wherein the first and second twisted portions are formed by a heat setting the one or more of the plurality of strut members.

8. The occlusive implant of claim 1, wherein the expandable framework comprises a shape-memory material.

9. The occlusive implant of claim 1, wherein in the expanded configuration, the expandable framework defines an enclosed volume.

10. An occlusive implant, comprising:
an expandable framework configured to shift between a collapsed configuration and an expanded configuration, wherein the expandable framework includes a plurality of strut members circumferentially spaced around a longitudinal axis of the expandable framework, wherein one or more of the plurality of strut members includes a first twisted portion, a second twisted portion, and a face portion extending therebetween, wherein in the expanded configuration, an entirety of the face portion extends linearly between the first twisted portion and the second twisted portion;
a plurality of fixation members disposed along the face portion of one or more of the plurality of strut members, each fixation member having a first end fixed to the strut member and a second free end extending radially away from the strut member; and
an occlusive member disposed along an outer surface of the expandable framework;
wherein in the collapsed configuration, a first plurality of fixation members disposed along a first face portion are longitudinally offset and circumferentially interdigitated with a second plurality of fixation members disposed along an adjacent second face portion.

11. The occlusive implant of claim 10, wherein the plurality of fixation members and the expandable framework are formed from a unitary tubular member.

12. The occlusive implant of claim 10, wherein an entirety of one or more of the plurality of fixation members defines a curve.

13. The occlusive implant of claim 10, wherein each of the plurality of strut members includes four or more fixation members disposed thereon.

14. The occlusive implant of claim 10, wherein the second free end of one or more of the plurality of fixation members defines a point.

15. The occlusive implant of claim 10, wherein the occlusive member extends circumferentially around the outer surface of the occlusive member.

16. The occlusive implant of claim 10, wherein at least a portion of the plurality of fixation members extend through an aperture formed in the occlusive member.

17. The occlusive implant of claim 10, wherein in the expanded configuration, the expandable framework defines an enclosed volume.

18. An occlusive implant, comprising:
an expandable framework configured to shift between a collapsed configuration and an expanded configuration, wherein the expandable framework includes a plurality of strut members circumferentially spaced around a longitudinal axis of the expandable framework, wherein some of the plurality of strut members include a first twisted portion, a second twisted portion, and a face portion extending therebetween, wherein in the expanded configuration, the first and second twisted portions on a first strut member twist in a first direction, and the first and second twisted portions on a second strut member twist in a second direction opposite the first direction, wherein the first and second strut members are adjacent one another; and
a plurality of fixation members disposed along the face portion of one or more of the plurality of strut members.

19. The occlusive implant of claim 18, wherein the expandable framework comprises a shape-memory material.

20. The occlusive implant of claim 18, wherein in the expanded configuration, the expandable framework defines an enclosed volume.

* * * * *